(12) United States Patent
Lin et al.

(10) Patent No.: US 9,927,359 B1
(45) Date of Patent: Mar. 27, 2018

(54) GAS DETECTION DEVICE

(71) Applicant: RADIANT INNOVATION INC., Hsinchu (TW)

(72) Inventors: Tseng-Lung Lin, Hsinchu (TW); Shao-Yun Yu, Hsinchu (TW); Yu-Tai Sung, Hsinchu (TW)

(73) Assignee: RADIANT INNOVATION INC., Hsinchu (TW)

( * ) Notice: Subject to any disclaimer, the term of this patent is extended or adjusted under 35 U.S.C. 154(b) by 0 days.

(21) Appl. No.: 15/274,629

(22) Filed: Sep. 23, 2016

(51) Int. Cl.
*G01N 21/59* (2006.01)
*G01N 33/00* (2006.01)

(52) U.S. Cl.
CPC ........... *G01N 21/59* (2013.01); *G01N 33/004* (2013.01); *G01N 2201/061* (2013.01)

(58) Field of Classification Search
CPC .................................................... G01N 21/59
See application file for complete search history.

(56) References Cited

U.S. PATENT DOCUMENTS 5,453,620 A * 9/1995 Wadsworth ........ G01N 21/3504
250/343
2014/0367574 A1* 12/2014 Lin ..................... G01N 21/3504
250/343

* cited by examiner

*Primary Examiner* — David Porta
*Assistant Examiner* — Hugh H Maupin
(74) *Attorney, Agent, or Firm* — Li & Cai Intellectual Property (USA) Office

(57) ABSTRACT

The instant disclosure provides a gas detection device including a chamber module, a light emitting module and an optical sensing module. The chamber module comprises a light condensing chamber, a receiving chamber and a sampling chamber connected between the light condensing chamber and the receiving chamber. The light emitting module is disposed on the light condensing chamber for generating a light. The optical sensing module is disposed in the receiving chamber. The sampling chamber comprises a first open end, a second open end corresponding to the first open end, a first surface, and a second surface corresponding to the first surface, the first and second open ends are connected to the light condensing chamber and the receiving chamber respectively, the first surface and the second surface are disposed between the first open end and the second open end, and the first surface is not parallel to the second surface.

17 Claims, 13 Drawing Sheets

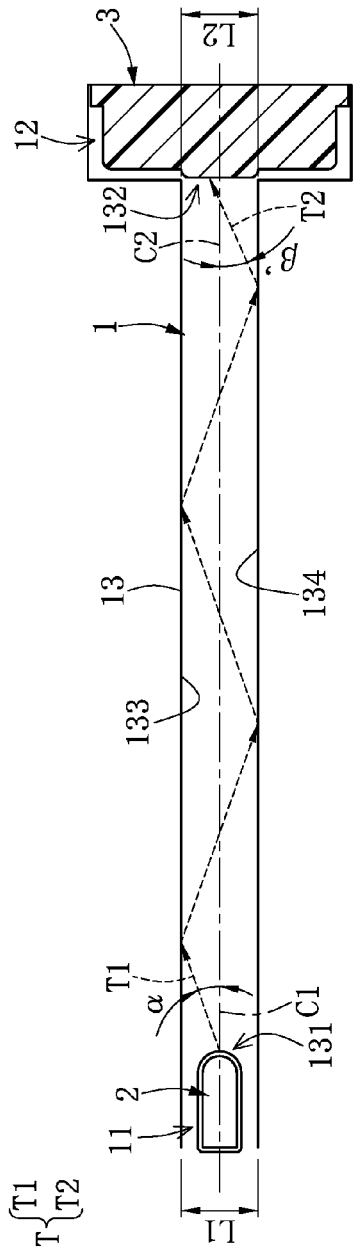
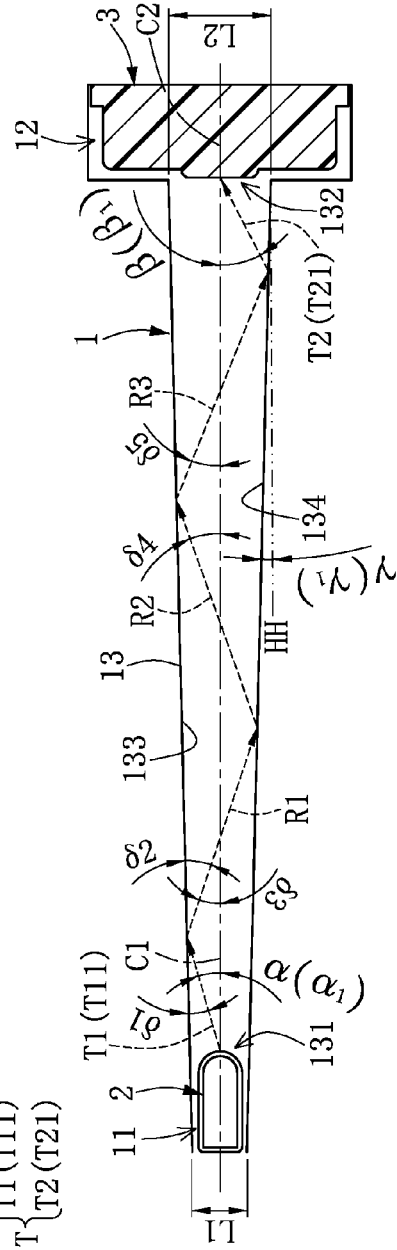
FIG. 4
FIG. 5

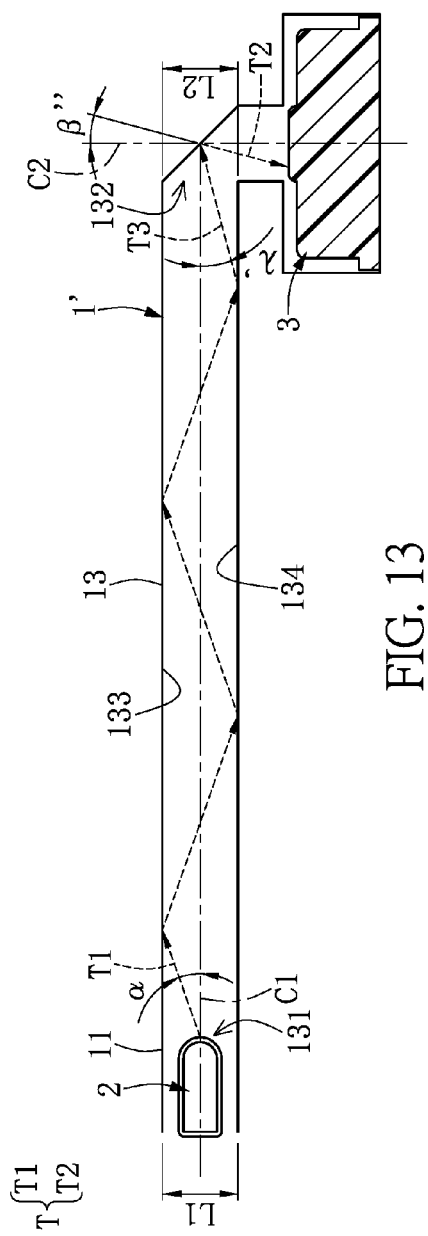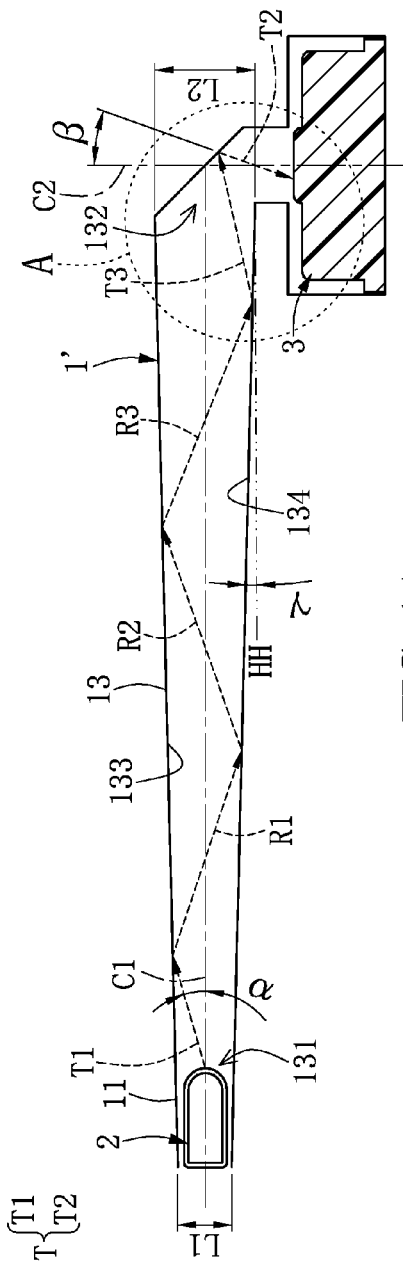

GAS DETECTION DEVICE

BACKGROUND

1. Technical Field

The instant disclosure relates to a gas detection device, in particular, to a gas detection device for detecting the concentration of a gas.

2. Description of Related Art

The carbon dioxide detection devices or carbon dioxide analyzing instruments in the market generally employ non-dispersive infrared (NDIR) absorption to detect the concentration of the gas. The NDIR mainly uses a calculation based on the Beer-Lambert law. The principle of such analysis is to detect the concentration of a specific gas by using the absorption property of the gas toward infrared light having a specific wavelength and the fact that the gas concentration is proportional to the absorption quantity. For example, carbon monoxide has a strongest absorption to a wavelength of 4.7 micron ($\mu m$) and carbon dioxide has a strongest absorption to a wavelength of 4.3 micron ($\mu m$).

However, the accuracy of the gas concentration detecting devices are limited to the structure of the gas sampling chamber, and hence, the amount of the infrared light projected onto the infrared sensor is decreased and the accuracy of the detection is reduced.

Regarding the conventional infrared light sensor, when the incident light projected onto the infrared light sensor is larger than 20 degrees, the specific band width of the filter plate leads the peak value of the filter plate to deviate 40 nanometers (nm) toward the shorter wavelength. Therefore, a part of the light which is not light that can be absorbed by the gas to be measured will be projected onto the infrared light sensor, and another part of the light related to the gas to be measured is blocked, thereby reducing the intensity of the signal and reducing the detection accuracy. However, 20 degrees is only an example and the infrared light sensor can have preferably an angle other than 20 degrees in other embodiments.

Therefore, there is a need for increasing the detection accuracy of the gas concentration detection device for overcome the above disadvantage.

SUMMARY

The instant disclosure provides a gas detection device adapting inner surfaces that are not parallel to each other in the sampling chamber, thereby effectively increasing the detection accuracy of the gas concentration.

An embodiment of the present disclosure provides a gas detection device, comprising a chamber module, a light emitting module and an optical sensing module. The chamber module comprises a condensing chamber, a receiving chamber and a sampling chamber connected between the condensing chamber and the receiving chamber. The light emitting module is disposed on the condensing chamber for generating a light. The optical sensing module is disposed in the receiving chamber. The sampling chamber comprises a first open end, a second open end opposite to the first open end, a first surface and a second surface opposite to the first surface, the first open end is connected to the condensing chamber, the second open end is connected to the receiving chamber, the first surface and the second surface are disposed between the first open end and the second open end, and the first surface and the second surface are not parallel to each other.

Another embodiment of the instant disclosure provides a gas detection device comprising a chamber module, a light emitting module and an optical sensing module. The chamber module comprises a light condensing chamber, a receiving chamber and a sampling chamber connected between the light condensing chamber and the receiving chamber. The light emitting module is disposed on the light condensing chamber for generating a light. The optical sensing module is disposed in the receiving chamber. The sampling chamber comprises a first open end, a second open end opposite to the first open end, a first surface, a second surface opposite to the first surface, a third surface and a fourth surface opposite to the third surface. The first open end is connected to the light condensing chamber, the second open end is connected to the receiving chamber, the first surface, the second surface, the third surface and the fourth surface are disposed between the first open end and the second open end and are connected to each other sequentially, the first surface is not parallel to the second surface, and the third surface is not parallel to the fourth surface.

The advantage of the instant disclosure is that based on the technical feature of disposing the first surface and the second surface between the first open end and the second open end, and the design where the first surface and the second surface are not parallel to each other, the gas detection device provided by the instant disclosure can effectively increase the detection accuracy of the gas concentration.

In order to further understand the techniques, means and effects of the instant disclosure, the following detailed descriptions and appended drawings are hereby referred to, such that, and through which, the purposes, features and aspects of the instant disclosure can be thoroughly and concretely appreciated; however, the appended drawings are merely provided for reference and illustration, without any intention to be used for limiting the instant disclosure.

BRIEF DESCRIPTION OF THE DRAWINGS

The accompanying drawings are included to provide a further understanding of the instant disclosure, and are incorporated in and constitute a part of this specification. The drawings illustrate exemplary embodiments of the instant disclosure and, together with the description, serve to explain the principles of the instant disclosure.

FIG. 4 is one of the light projection schematic views of the gas detection device of the first embodiment of the instant disclosure.

FIG. 5 is another light projection schematic view of the gas detection device of the first embodiment of the instant disclosure.

FIG. 13 is one of the light projection schematic views of the gas detection device of the first embodiment of the instant disclosure.

FIG. 14 is another light projection schematic view of the gas detection device of the first embodiment of the instant disclosure.

DESCRIPTION OF THE EXEMPLARY EMBODIMENTS

Figure 1:
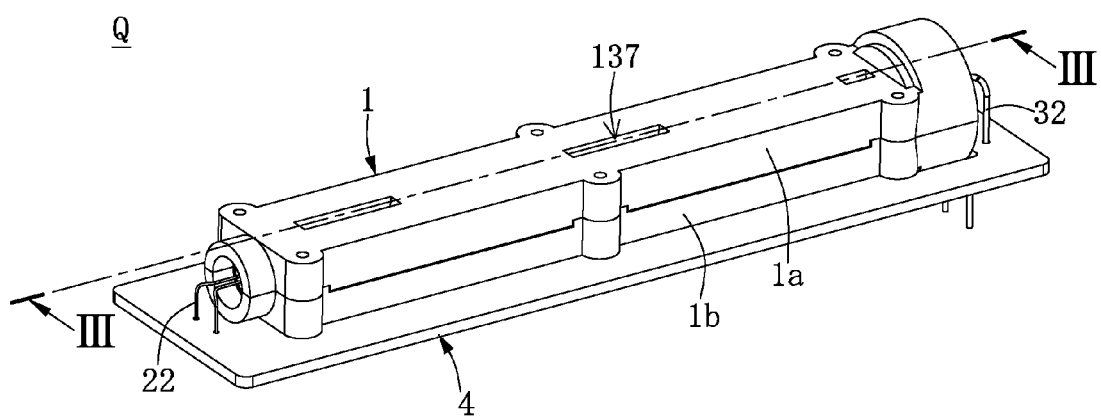
FIG. 1 is one of the three-dimensional assembly schematic views of the gas detection device of the first embodiment of the instant disclosure.

Reference will now be made in detail to the exemplary embodiments of the instant disclosure, examples of which are illustrated in the accompanying drawings. Wherever possible, the same reference numbers are used in the drawings and the description to refer to the same or like parts.

First Embodiment

Figure 2:
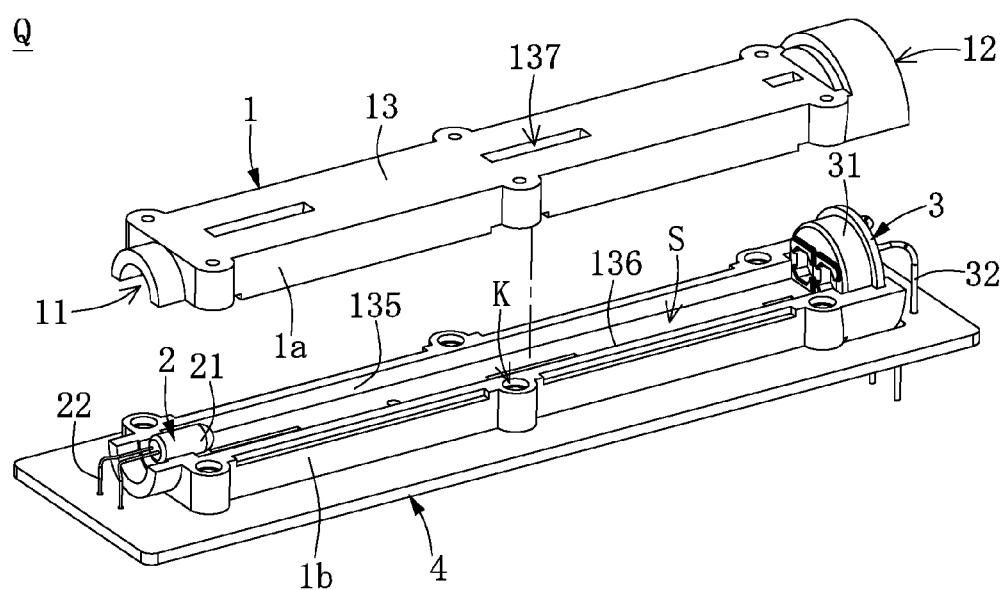
FIG. 2 is one of the three-dimensional exploded schematic views of the gas detection device of the first embodiment of the instant disclosure.

Please refer to FIG. 1 and FIG. 2. The first embodiment of the instant disclosure provides a gas detection device Q comprising a chamber module, a light emitting module 2, an optical sensing module 3 and a substrate module 4. The light emitting module 2 and the optical sensing module 3 can be electrically connected to the substrate module 4. In addition, the substrate module 4 can be electrically connected to a display unit (not shown), a control unit (not shown) and a processing unit (not shown). For example, the light emitting module 2 is an infrared light emitter generating infrared light and the optical sensing module 3 is an infrared light sensor such as a single-channel infrared light sensor or a double-channel infrared light sensor (in which one of the infrared light collecting windows is used to detect the gas concentration and the other is used to detect the aging of the infrared light source, and the two windows can calibrate each other). However, the instant disclosure is not limited thereto.

The gas detection device Q provided by the instant disclosure can detect the concentration or other properties of the gas to be detected. The gas to be detected can be carbon dioxide, carbon monoxide or the combination thereof. The instant disclosure is not limited thereto. Based on the selection of different light emitting modules 2 and optical sensing modules 3, different gases can be measured. For example, regarding concentration detection, different types of gases can be detected by changing the wavelength filter (filter plate) on the optical sensing module 3.

Figure 3:
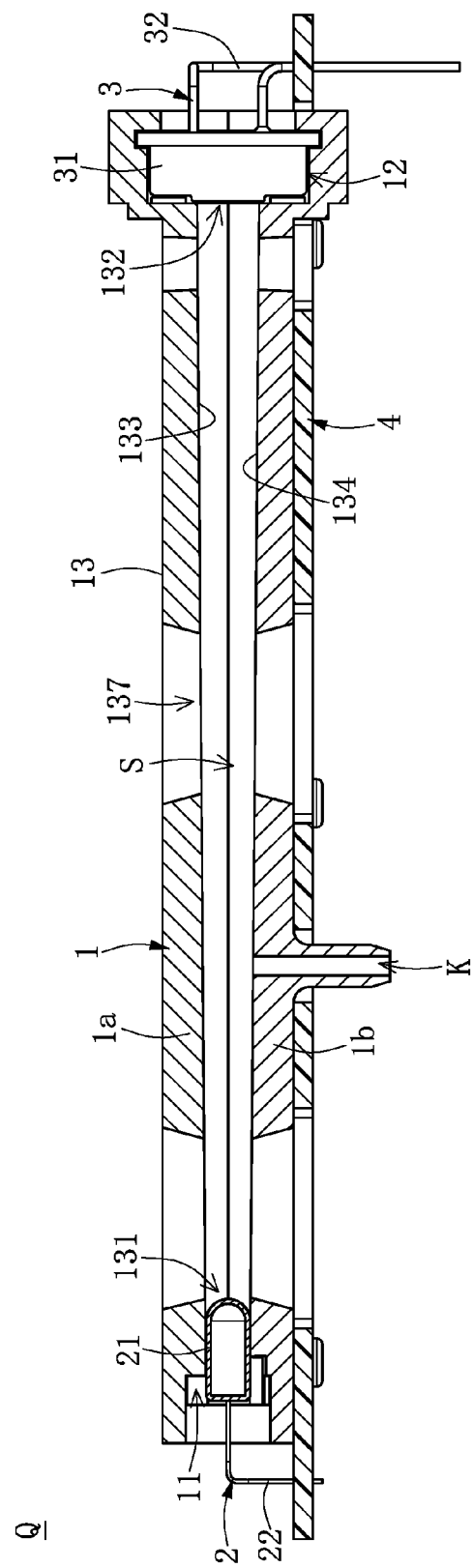
FIG. 3 is the sectional schematic view taken from line III-III in FIG. 1.

Please refer to FIG. 3. The chamber module has a sampling space S, and the chamber module comprises a condensing chamber 11, a receiving chamber 12 and a sampling chamber 13 connecting the condensing chamber 11 and the receiving chamber 12. The light emitting module 2 is disposed on the condensing chamber 11 for generating light T such as infrared light. The optical sensing module 3 comprises an optical sensing unit 31 disposed in the receiving chamber 12 for receiving light T generated by the light emitting unit 21.

As shown in FIG. 1 to FIG. 3, the chamber module 1 is constituted by the upper chamber module 1a and the lower chamber module 1b for facilitating the assembly of the chamber module 1. For example, the upper chamber module 1a and the lower chamber module 1b can be assembled with each other by fixing members (not shown) such as screws in the fixing holes K. The chamber module 1 can be fixed on the substrate module 4 by fixing the chamber module 1 through fixing members (not shown) into the fixing holes K. In the embodiments of the instant disclosure, the substrate module 4 is a printed circuit board (PCB), the light emitting module 2 further comprises a connecting line 22, and the optical sensing module 3 further comprises a connecting line 32. The connecting line 22 of the light emitting module 2 and the connecting line 32 of the optical sensing module 3 can steadily fix the light emitting unit 21 and the optical sensing unit 31 on the substrate module 4 by soldering, thereby preventing the loose contact caused by external forces. The sampling space S in the sampling chamber 13 can have a cross section of a rectangular shape (in a direction perpendicular to the length direction of the sampling chamber 13). However, the instant disclosure is not limited thereto. In other words, in other embodiments, the cross section of the sampling space S in the sampling chamber 13 can be a pentagon, a hexagon or a polygon.

Please refer to FIG. 2 and FIG. 3. The sampling chamber 13 comprises a first open end 131, a second open end 132 opposite to the first open end 131, a first surface 133 (such as the upper surface), a second surface 134 opposite to the first surface 133 (such as the lower surface), a third surface 135 (such as the left side surface), and a fourth surface 136 opposite to the third surface 135 (such as the right side surface). The first open end 131 is connected to the condensing chamber, the second open end 132 is connected to the receiving chamber 12, the first surface 133, the second surface 134, the third surface 135 and the fourth surface 136 are disposed between the first open end 131 and the second open end 132. The first surface 133, the second surface 134, the third surface 135 and the fourth surface 136 are sequentially connected to each other and form the sampling space S. In the embodiments of the instant disclosure, the first surface 133 and the second surface 134 are not parallel to each other. The third surface 135 and the fourth surface 136 can be disposed in a way that the third surface 135 and the fourth surface 136 are not parallel to each other as well. However, the instant disclosure is not limited thereto.

Each of the first surface 133, the second surface 134, the third surface 135 and the fourth surface 136 can have a reflective layer thereon. The reflective layer is formed in the sampling chamber 13 by metal plating or plastic plating and is made of gold, nickel or the combination thereof. Therefore, the sampling chamber 13 having a rectangular shape is a rectangular optical integrator in which light T generated by the light emitting module 2 is repeatedly reflected in the sampling chamber 13, and the light intensity is integrated in the sampling chamber 13, thereby forming a uniform light distribution. In addition, the sampling chamber 13 further has one or more gas diffusing tanks 137 vertically penetrating the first surface 133 or the second surface 134 of the sampling chamber 13. The gas diffusing tank 137 can be disposed between the first open end 131 and the second open end 132 of the sampling chamber 13. In addition, the gas diffusing tank 137 can have a rectangular shape.

Please refer to FIG. 4 and FIG. 5. FIG. 4 shows an implementation in which the first surface 133 and the second surface 134 are parallel to each other, i.e., the implementation in the existing art. FIG. 5 shows an implementation in which the first surface 133 and the second surface 134 are not parallel to each other, i.e., the implementation of the instant disclosure. The effects of the two implementations toward the light path are discussed below. As shown in FIG. 4, the first surface 133 and the second surface 134 of the first open end 131 has a first predetermined distance L1 therebetween, and the first surface 133 and the second surface 134 of the second open end 132 has a second predetermined distance L2 therebetween. Since the first surface 133 and the second surface 134 are parallel to each other, the second predetermined distance L2 is equal to the first predetermined distance L1.

Light T generated by the light emitting unit 21 comprises a projection light T1 projected onto the first surface 133 and a received light T2, the projection light T1 is reflected by the first surface 133 and the second surface 134 and forms the received light T2 projected onto and received by the optical sensing unit 31. The light emitting module 2 has a first central axis C1 passing the light central point (not shown) of the light emitting unit 21. The optical sensing module 3 has a second central axis C2, the second central axis C2 can pass through the central point for receiving the light in the optical sensing module 3. In the first embodiment of the instant disclosure, the first central axis C1 and the second central axis C2 are parallel to each other and are coaxial. However, the instant disclosure is not limited thereto. In addition, the projection light T1 and the first central axis C1 has a projection angle α therebetween, and the received light T2 and the second central axis C2 has a receiving angle β' therebetween. Since the first predetermined distance L1 is equal to the second predetermined distance L2, i.e., the first surface 133 and the second surface 134 of the sampling chamber 13 are parallel to each other, when the projection angle α is 20 degrees, the receiving angle β' is 20 degrees.

Please refer to FIG. 5. The second predetermined distance L2 of the second open end 132 adjacent to the optical sensing module 3 is larger than the first predetermined distance L1 of the first open end 131 adjacent to the light emitting module 2. Specifically, the light T comprises a projection light T1 (or referred to as the first projection light T11) projected onto the first surface 133 and a received light T2 (or referred to as the first received light T21) received by the optical sensing module 3. The projection light T1 and the first central axis C1 have a projection angle α (or referred to as the first projection angle $α_1$) defined therebetween, the received light T2 and the second central axis C2 have a receiving angle β (or referred to as the first receiving angle β1) defined therebetween. In the embodiments of the instant disclosure, the first central axis C1 can be parallel to a horizontal axis HH.

Please refer to FIG. 5. In the embodiments of the instant disclosure, the slope of the first surface 133 adjacent to the first open end 131 is equal to the slope of the first surface 133 adjacent to the second open end 132, and the slope of the second surface 134 adjacent to the first open end 131 is equal to the slope of the second surface 134 adjacent to the second open end 132. The projection light T1 is reflected N times between the first surface 133 and the second surface 134. An inclined angle γ is defined between the first surface 133 and the horizontal axis HH and between the second surface 134 and the horizontal axis HH respectively. The receiving angle β between the received light T2 and the second central axis C2 satisfies the relationship of $β=α-2γN$, wherein α is the projection angle, β is the receiving angle, γ is the inclined angle, and N is the number of the times of reflection. In the embodiments of the instant disclosure, the inclined angle γ is between 0.1 degree to 5 degrees, preferably is between 0.3 degree to 3 degrees, more preferably is 0.5 degree. However, the instant disclosure is not limited thereto.

In addition, the projection light T1 is reflected by the first surface 133 and the second surface 134 for forming M reflected lights reflected between the first surface 133 and the second surface 134 (such as the first reflective light R1, the second reflective light R2 and the third reflective light R3), and the angle between the $M^{th}$ reflected light and the first central axis C1 is smaller than the angle between the $(M-1)^{th}$ reflected light and the first central axis C1. In other words, since both of the first surface 133 and the second surface 134 have an inclined angle γ relative to the first central axis C1, the angle between a reflected light and the first central axis C1 will be larger than the angle between the previous reflected light and the first central axis C1.

For example, when the projection angle α between the projection light T1 and the first central axis C1 is 20 degrees, and the inclined angle γ is 0.5 degree, the first angle δ1 between the projection light T1 and the first surface 133 can be 19.5 degrees. The projection light T1 is reflected by the first surface 133 and forms a first reflective light R1 projected onto the second surface 134. Based on the law of reflection, the second angle δ2 between the first reflective light R1 and the first central axis C1 is 19.5 degrees, and the third angle δ3 between the first reflective light R1 and the first central axis C1 is 19 degrees. The first reflective light R1 is reflected by the second surface 134 and forms a second reflective light R2 projected onto the first surface 133. The fourth angle M between the second reflective light R2 and the first central axis C1 is 18 degrees. The second reflective light R2 is reflected by the first surface 133 and forms a third reflective light R3 projected onto the second surface 134. The fifth angle 65 between the third reflective light R3 and the first central axis C1 is 17 degrees. The third reflective light R3 is reflected by the second surface 134 and forms a received light T2 projected onto and received by the optical sensing module 3. The receiving angle β between the received light T2 and the first central axis C1 is 16 degrees.

In the first embodiment of the instant disclosure, the first central axis C1 and the second central axis C2 are coaxial and hence, the receiving angle β between the received light T2 and the second central axis C2 is 16 degrees. In addition, the reflection time of the projection light T1 by the first surface 133 and the second surface 134 is 4 times (the total counts of the projection light T1 contacts the first surface 133 and the second surface 134). In other words, based on the equation $β=α-2γN$, the receiving angle β is 20−(2*0.5*4) degrees, i.e., 16 degrees. The included angle between the second reflective light R2 and the first central axis C1 will be smaller than the included angle between the first reflective light R1 and the first central axis C1.

Compared to the condition that the first predetermined distance L1 and the second predetermined distance L2 are equal, the condition that the second predetermined distance L2 is larger than the first predetermined distance L1 can receive more infrared light. In other words, the received light T2 preferably enters the optical sensing unit 31 in a vertical direction. In addition, the projection angle α of 20 degrees is only an example, and the instant disclosure is not limited thereto. In other words, different optical sensing modules 3 can have different preferable receiving angles β. In the embodiments of the instant disclosure, the distance between the first open end 131 and the second open end 132

(i.e., the length of the sampling chamber 13) can be 35 millimeter (mm) to 50 mm. However, the instant disclosure is not limited thereto.

Figure 6:
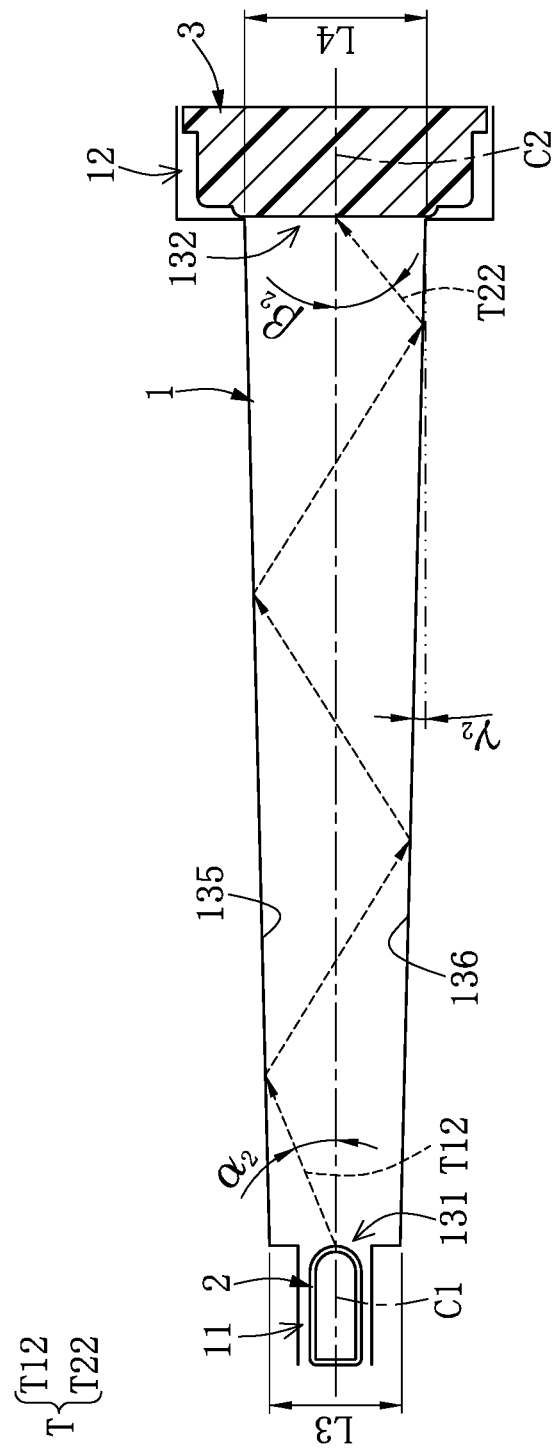
FIG. 6 is yet another light projection schematic view of the gas detection device of the first embodiment of the instant disclosure.
Figure 7:
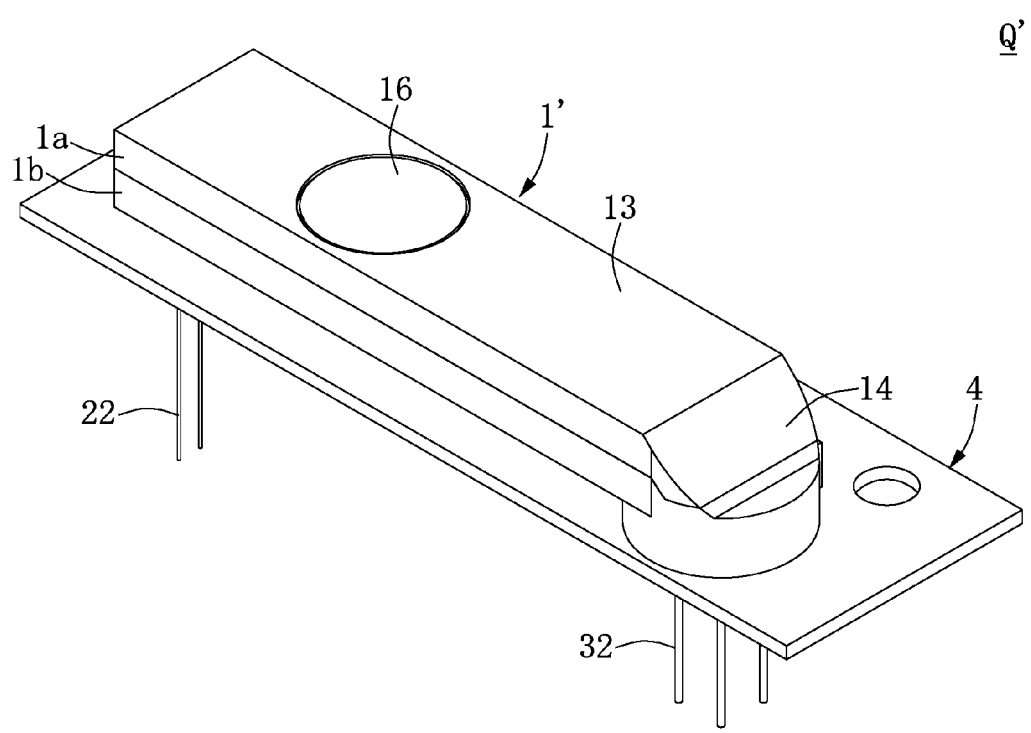
FIG. 7 is one of the three-dimensional assembly schematic views of the gas detection device of the second embodiment of the instant disclosure.
Figure 8:
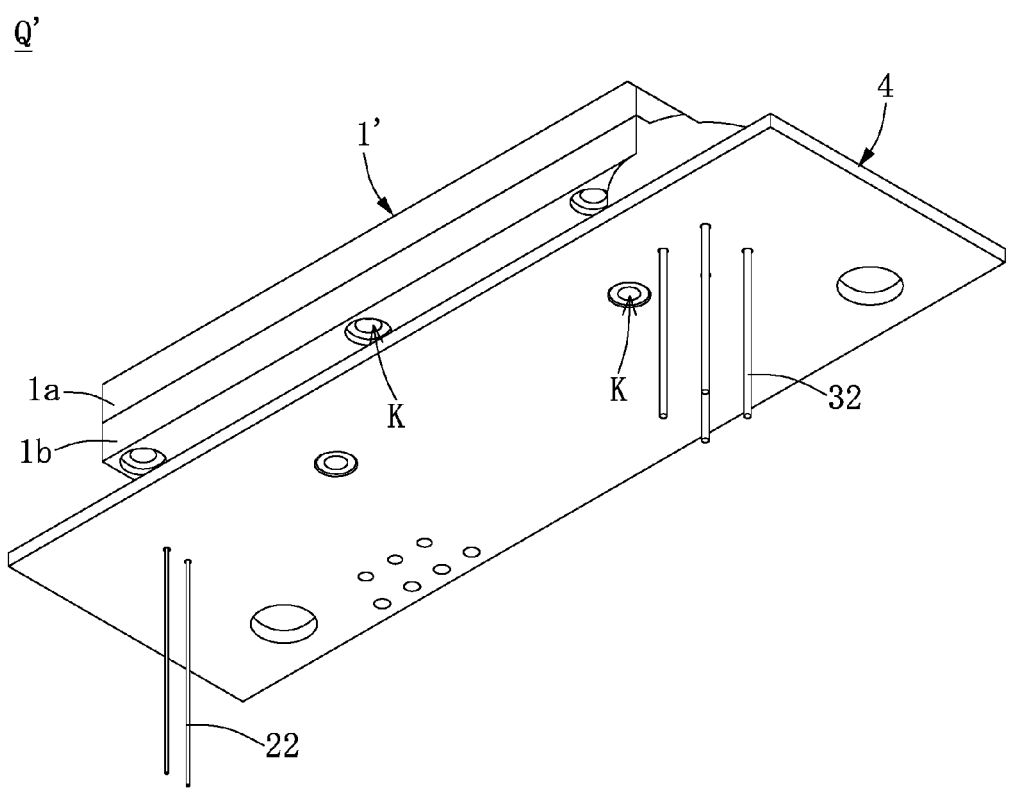
FIG. 8 is another three-dimensional assembly schematic view of the gas detection device of the second embodiment of the instant disclosure.
Figure 9:
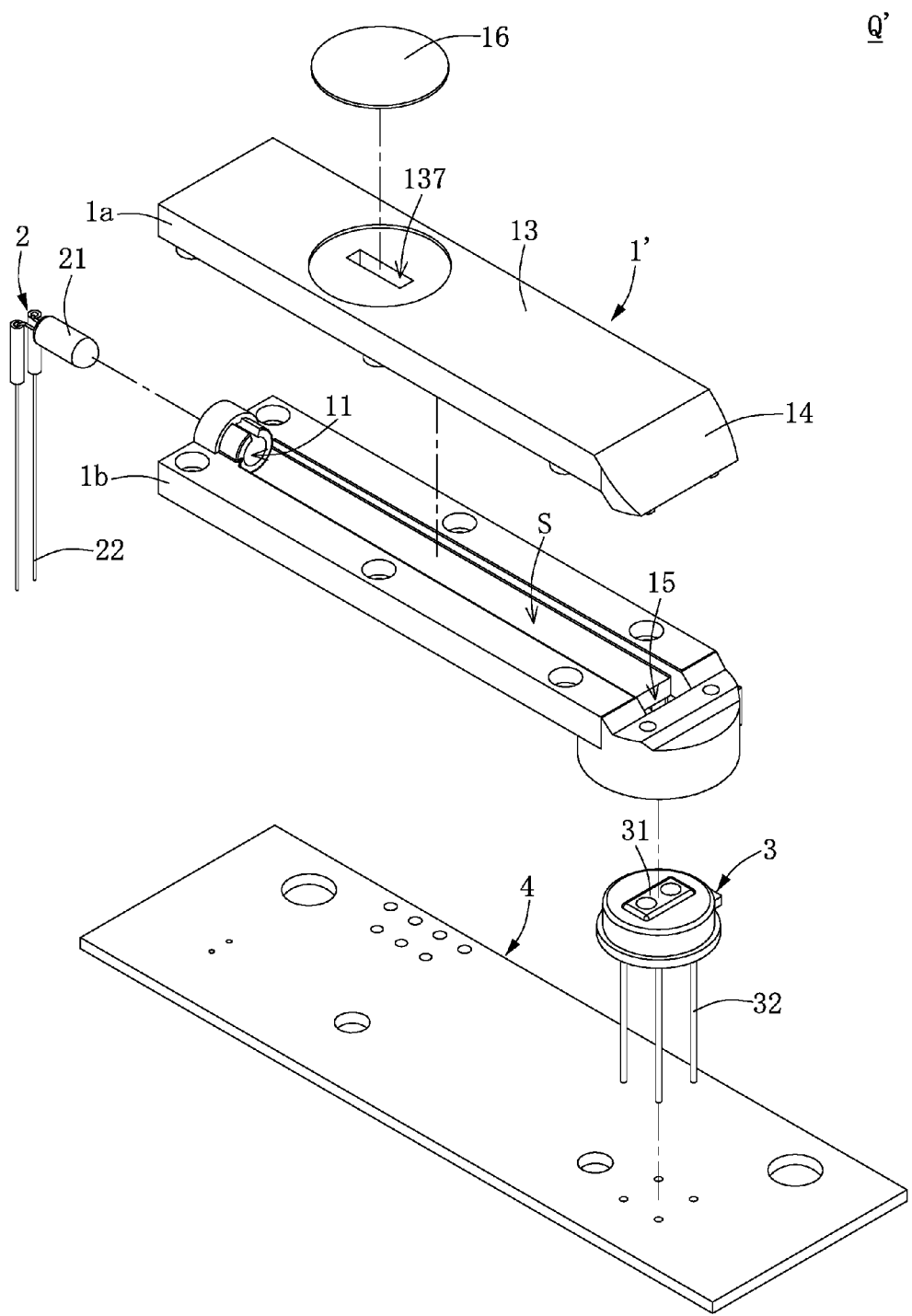
FIG. 9 is one of the three-dimensional exploded schematic views of the gas detection device of the second embodiment of the instant disclosure.
Figure 10:
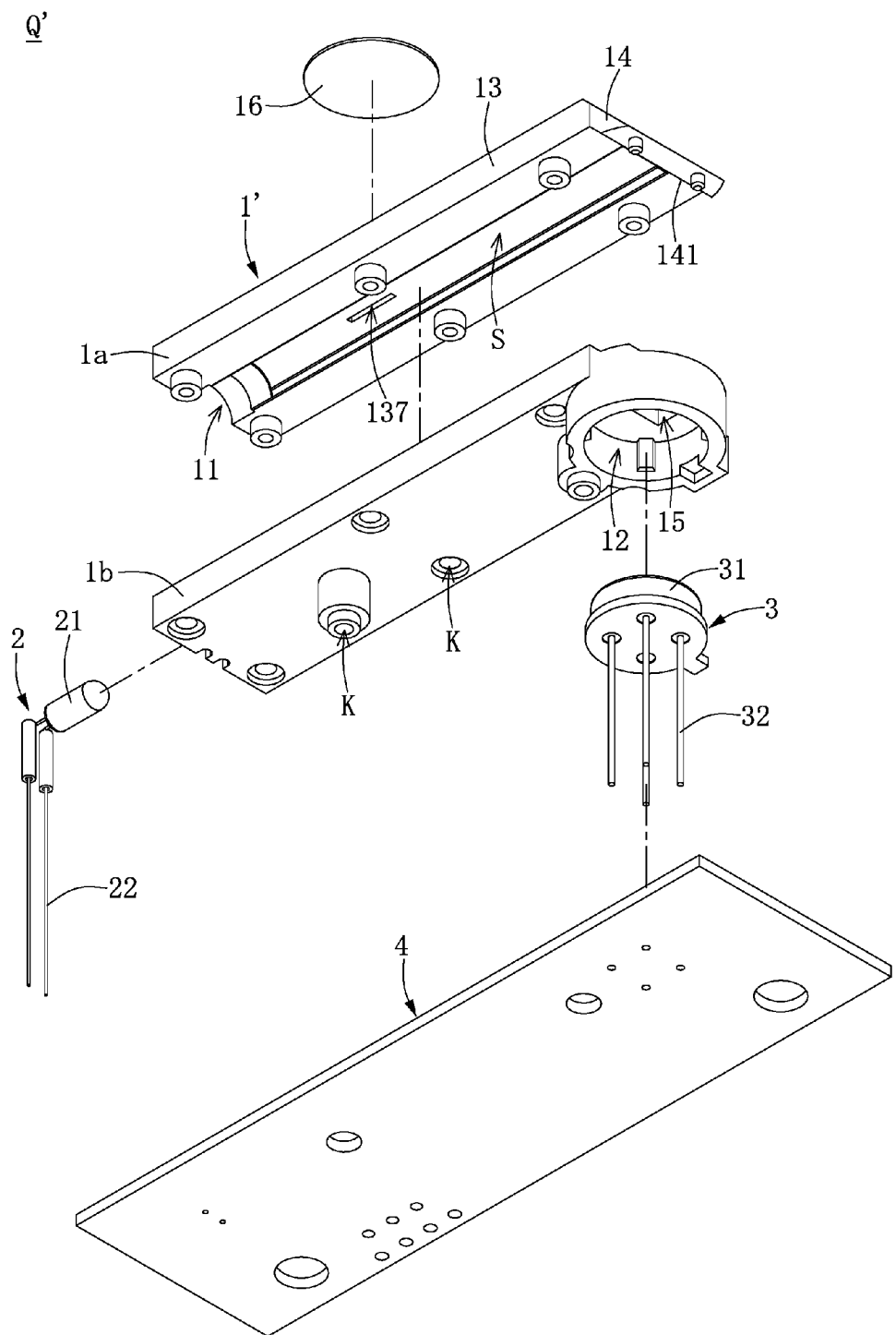
FIG. 10 is another three-dimensional exploded schematic view of the gas detection device of the second embodiment of the instant disclosure.
Figure 11:
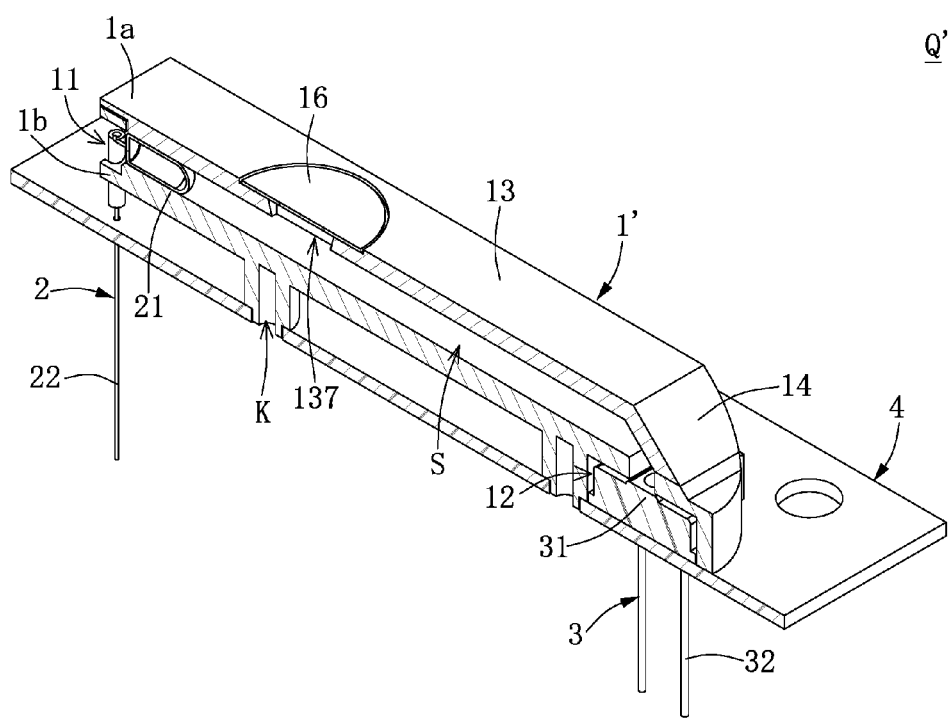
FIG. 11 is a three-dimensional sectional schematic view of the gas detection device of the second embodiment of the instant disclosure.

Please refer to FIG. 6. In this embodiment, the third surface 135 and the fourth surface 136 are inclined relative to the first central axis C1, i.e., the third surface 135 and the fourth surface 136 are not parallel to each other. Specifically, the third surface 135 and the fourth surface 136 of the first open end 131 have a third predetermined distance L3 defined therebetween, and the third surface 135 and the fourth surface 136 of the second open end 132 have a fourth predetermined distance L4 defined therebetween, and the fourth predetermined distance L4 is larger than the third predetermined distance L3.

Please refer to the description regarding FIG. 5 and FIG. 6. The light T comprises a first projection light T11 projected onto the first surface 133 and a second projection light T12 projected onto the third surface 135. The first projection light T11 is reflected by the first surface 133 and the second surface 134 and forms a first received light T21 projected onto and received by the optical sensing module 3. The second projection light T12 is reflected by the third surface 135 and the fourth surface 136 for forming a second projection light T12 projected onto and received by the optical sensing module 3. The light emitting module 2 has a first central axis C1, and a first projection angle α1 is defined between the first projection light T11 and the first central axis C1. A second projection angle α2 is defined between the second projection light T12 and the first central axis C1. The optical sensing module 3 has a second central axis C2, and a first receiving angle β1 is defined between the first received light T21 and the second central axis C2. The first receiving angle β2 is defined between the second received light T22 and the second central axis C2.

The first projection light T11 is reflected $N_1$ times between the first surface 133 and the second surface 134, and the second projection light T12 is reflected for $N_2$ times between the third surface 135 and the fourth surface 136. The first central axis C1 and the second central axis C2 are both parallel to a horizontal axis HH. A first inclined angle $\gamma_1$ is defined between the first surface 133 and the horizontal axis HH, and between the second surface 134 and the horizontal axis HH. A second inclined angle $\gamma_2$ is defined between the third surface 135 and the horizontal axis HH, and between the fourth surface 136 and the horizontal axis HH. The first receiving angle $\beta_1$ between the first received light T21 and the second central axis C2 satisfy the following relationship: $\beta_1=\alpha_1-2\gamma_1 N_1$. The first receiving angle $\beta_2$ between the second received light T22 and the second central axis C2 satisfy the following relationship: $\beta_2=\alpha_2-2\gamma_2 N_2$. first projection angle α1 is the value of the first projection angle, second projection angle $\alpha_2$ is the value of the second projection angle, first receiving angle $\beta_1$ is the first receiving angle, first receiving angle $\beta_2$ is the second receiving angle, first inclined angle $\gamma_1$ is the first inclined angle, second inclined angle $\gamma_2$ is the second inclined angle, $N_1$ is the times of reflection of the first projection light T11 between the first surface 133 and the second surface 134, and $N_2$ is the number of times of reflection of the second projection light T12 between the first surface 133 and the second surface 134.

The reflection patterns of the second projection light T12 between the third surface 135 and the fourth surface 136 are similar to that of the first projection light T11 between the first surface 133 and the second surface 134 and hence, the details are not described herein. Therefore, the implementation of the second projection angle $\alpha_2$, the first receiving angle $\beta_2$ and the second inclined angle $\gamma_2$ are similar to that of the first projection angle $\alpha_1$, the first receiving angle $\beta_1$ and the first inclined angle $\gamma_1$. However, since the sampling space S of the sampling chamber 13 is a rectangular cross section, the third predetermined distance L3 is larger than the first predetermined distance L1 and the fourth predetermined distance L4 is larger than the second predetermined distance L2, the second inclined angle $\gamma_2$ can be between 0.1 degree to 5 degrees, preferably between 1 degree to 3 degrees, more preferably 1.5 degrees. However, the instant disclosure is not limited thereto.

The Second Embodiment

Please refer to FIG. 7 to FIG. 11. The second embodiment of the instant disclosure provides a gas detection device Q' comprising a chamber module 1', a light emitting module 2, an optical sensing module 3 and a substrate module 4. Based on the comparison between FIG. 7 and FIG. 1, it is shown that the main difference between the second embodiment and the first embodiment comprises that the chamber module 1' provided by the second embodiment is different from the chamber module 1 provided by the first embodiment, and the arrangement of the optical sensing module 3 of the second embodiment is different from that of the first embodiment.

Figure 12:
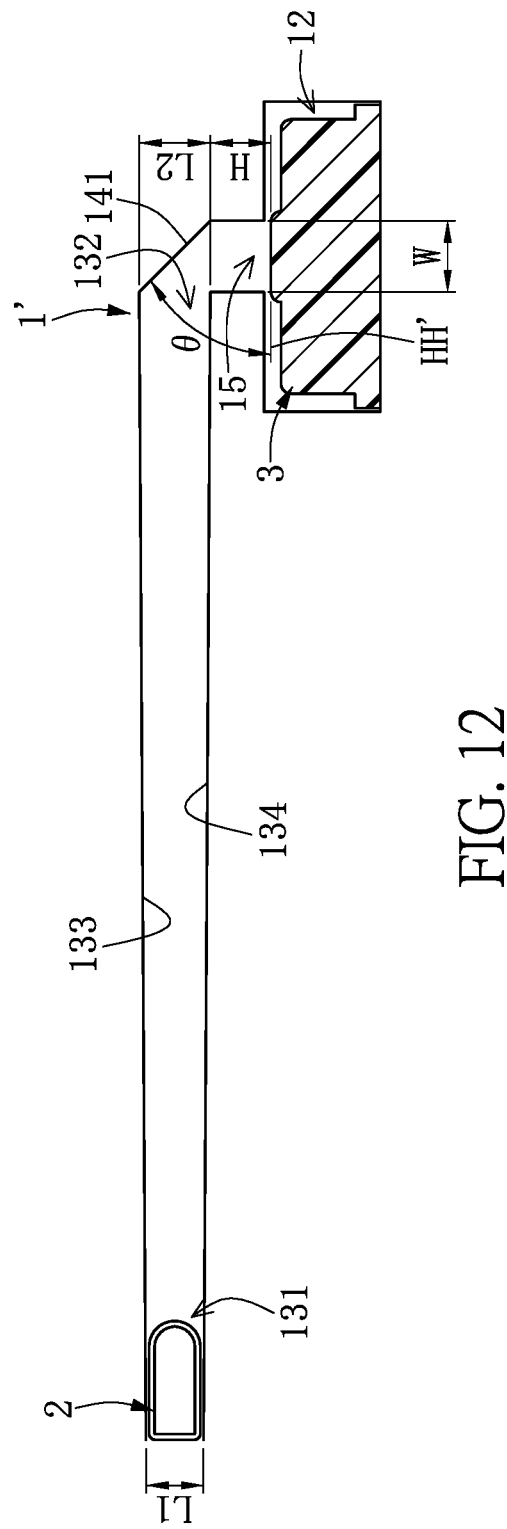
FIG. 12 is a side schematic view of the gas detection device of the second embodiment of the instant disclosure.

Specifically, the chamber module 1' further comprises a light guiding portion 14 disposed between the sampling chamber 13 and the receiving chamber 12, the light guiding portion 14 has a light guiding surface 141, the light guiding surface 141 reflects the projection light T1 generated by the light emitting unit 21 into the optical sensing unit 31. For example, the light guiding surface 141 has a reflective layer mentioned before (not shown) coated thereon, or the light guiding surface 141 is a reflective mirror. The instant disclosure is not limited thereto. In addition, the chamber module 1' can further comprise an open slot 15 connected between the light guiding portion 14 and the receiving chamber 12. The second surface 134 of the sampling chamber 13 and the optical sensing unit 31 have a predetermined height H (as shown in FIG. 12) defined therebetween. Therefore, the light path of the light generated by the light emitting unit 21 is in a substantially "L" shape which starts from the light emitting unit 21 to the optical sensing unit 31.

The chamber module 1' further comprises a gas filtering membrane 16 disposed on the gas diffusing tank 137. For example, the gas filtering membrane 16 is a waterproof and air permeable membrane for avoiding the suspended particles from entering the chamber module 1', thereby preventing the pollution in the chamber module 1' and ensuring the detection accuracy. The other structures of the second embodiment are similar to that of the first embodiment and are not described in detail herein.

Please refer to FIG. 12. In the second embodiment of the instant disclosure, the light guiding portion 14 is connected between the second open end 132 and the receiving chamber 12, and the light guiding surface 141 of the light guiding portion 14 inclines for a predetermined angle θ of from 30 to 60 degrees relative to the first central axis C1 or the horizontal axis HH' (the first central axis C1 is parallel to the horizontal axis HH'), or the light guiding surface 141 of the light guiding portion 14 inclines for a predetermined angle θ of from 30 to 60 degrees relative to the surface of the optical sensing unit 31. Preferably, the predetermined angle θ is 45 degrees. In other words, the surface of the optical sensing unit 31 and the horizontal axis HH are parallel to each other. In addition, preferably, the open slot 15 is connected between the light guiding portion 14 and the receiving chamber 12. In FIG. 12, the open slot 15 has a predetermined width W and the second surface 134 adjacent to the second open end 132 and the optical sensing unit 31 have a predetermined height H defined therebetween, and the predetermined width W and the predetermined height H satisfy the following equation: (0.8*W)≤H≤(3*W), in which H is the predetermined height, and W is the predetermined width. In addition, the predetermined height H and the second predetermined distance L2 satisfy the following equation: (0.8*L2)≤H≤(3*L2), in which H is the predetermined height, and L2 is the second predetermined distance. In other words, the predetermined width W can be equal to the second predetermined distance L2.

For example, in the embodiments of the instant disclosure, the cross section of the rectangular sampling chamber 13 (the cross section of the sampling space S) can be larger than or equal to the sensing area of the optical sensing unit 31. In addition, since the size of the existing double-channel infrared light sensor is about 4 mm*2 mm, the second predetermined distance L2 can be 2.1 mm, and the predetermined width W can be equal to the second predetermined distance L2. However, the instant disclosure is not limited thereto. In other embodiments, the predetermined width W can be from (1.1*L2) to (2.3*L2). The predetermined height H can be from 1 mm to 2 mm, preferably 1.5 mm. However, the instant disclosure is not limited thereto.

Figure 15:
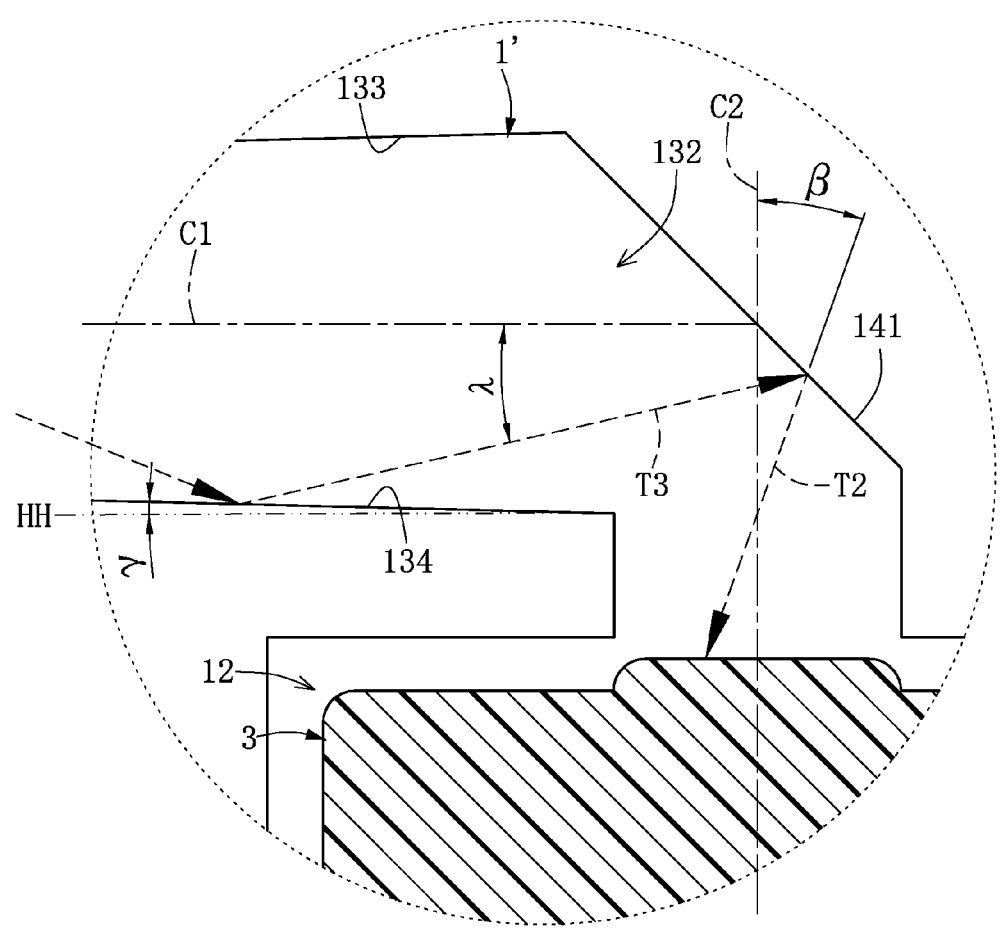
FIG. 15 is an enlargement view of part A of FIG. 14.

Please refer to FIG. 13 to FIG. 15. FIG. 13 shows the implementation in which the first surface 133 and the second surface 134 are parallel to each other, i.e., the first predetermined distance L1 is equal to the second predetermined distance L2. FIG. 14 shows the implementation in which the first surface 133 and the second surface 134 are not parallel to each other, i.e., the first predetermined distance L1 and the second predetermined distance L2 are different from each other. The results achieved by the two implementations are described below.

The implementation of FIG. 13 is discussed under the condition that the predetermined angle θ of the light guiding surface 141 is 45 degrees. Specifically, the light T comprises a projection light T1 projected onto the first surface 133, the projection light T1 is reflected by the first surface 133 and the second surface 134 for forming an incident light T2 projected onto the light guiding surface 141. The incident light T2 is reflected by the light guiding surface 141 for forming a received light T2 projected onto and received by the optical sensing module 3. The light emitting module 2 has a first central axis C1, and a projection angle α is defined between the projection light T1 and the first central axis C1. The optical sensing module 3 has a second central axis C2, a receiving angle β" is defined between the received light T2 and the second central axis C2, and an incident angle λ' is defined between the incident light T2 and the first central axis C1. In the second embodiment of the instant disclosure, the first central axis C1 and the second central axis C2 are perpendicular to each other. However, the instant disclosure is not limited thereto.

Please refer to the description regarding FIG. 4 set forth in the first embodiment. Since the first surface 133 and the second surface 134 are parallel to each other, the projection angle α between the projection light T1 and the first central axis C1 is equal to the incident angle λ between the incident light T2 and the first central axis C1. The incident light T2 is reflected by the light guiding surface 141 of 45 degrees and forms the received light T2 projected onto and received by the optical sensing module 3. The receiving angle β" between the received light T2 and the second central axis C2 will be equal to the projection angle α (since the first surface 133 and the second surface 134 are parallel to each other). In addition, the incident angle λ' will be equal to the projection angle α.

Next, please refer to FIG. 14, FIG. 15, and FIG. 5. In the following description, the predetermined angle θ is 45 degrees, the inclined angle γ is 0.5 degree, and the projection angle is 20 degrees. Specifically, the light T comprises a projection light T1 projected onto the first surface 133. The projection light T1 is reflected by the first surface 133 and the second surface 134 to form an incident light T2 projected onto the light guiding surface 141. The incident light T2 is reflected by the light guiding surface 141 to form a received light T2 projected onto and received by the optical sensing module 3. As described in the first embodiment regarding FIG. 5, after the reflection of the first surface 133 and the second surface 134, the inclined angle γ between the incident light T2 and the first central axis C1 is 16 degrees. The incident light T2 having an incident angle γ of 16 degrees is reflected by the light guiding surface 141 and forms a received light T2 having a receiving angle β of 16 degrees.

As described in the first embodiment, the light guiding surface 141 inclines for a predetermined angle θ relative to the horizontal axis HH, and the projection light T1 is reflected for N times between the first surface 133 and the second surface 134. The first central axis C1 is parallel to the horizontal axis HH and an inclined angle γ is defined between the first surface 133 and the horizontal axis HH, and the second surface 134 and the horizontal axis HH. The inclined angle γ between the incident light T2 and the first central axis C1 satisfies the following relationship: λ=α−2γN, wherein α is the projection angle, λ is the incident angle, γ is the inclined angle and N is the number of the times of reflection.

Therefore, compared to the situation that the first predetermined distance L1 is equal to the second predetermined distance L2, under the situation that the second predetermined distance L2 is larger than the first predetermined distance L1, the optical sensing module 3 receives more infrared light.

[Effectiveness of the Embodiments]

In summary, the advantage of the instant disclosure is that the gas detection device Q, Q' provided by the embodiments of the instant disclosure has increased accuracy based on the technical feature "the first surface 133 and the second surface 134 are disposed between the first open end 131 and the second open end 132, and the first surface 133 and the second surface 134 are not parallel to each other". In other words, based on the design that the second predetermined distance L2 is larger than the first predetermined distance L1, the light projected onto the optical sensing module 3 can have a receiving angle smaller than that of the projection angle α.

The above-mentioned descriptions represent merely the exemplary embodiment of the present disclosure, without any intention to limit the scope of the instant disclosure thereto. Various equivalent changes, alterations or modifications based on the claims of the instant disclosure are all consequently viewed as being embraced by the scope of the instant disclosure.

What is claimed is:
1. A gas detection device, comprising:
 a chamber module comprising a condensing chamber, a receiving chamber and a sampling chamber connected between the condensing chamber and the receiving chamber;

a light emitting module disposed on the condensing chamber for generating a light; and an optical sensing module disposed in the receiving chamber;

wherein the sampling chamber comprises a first open end, a second open end opposite to the first open end, a first surface and a second surface opposite to the first surface, the first open end is connected to the condensing chamber, the second open end is connected to the receiving chamber, the first surface and the second surface are disposed between the first open end and the second open end, the first surface and the second surface are not parallel to each other;

wherein the light comprises a projection light projected onto the first surface;

wherein the light emitting module has a first central axis;

wherein the projection light is reflected by the first surface and the second surface to form M reflecting lights reflected between the first surface and the second surface, and an included angle between the $M^{th}$ reflecting light and the first central axis is smaller than an included angle between the $(M-1)^{th}$ reflecting light and the first central axis.

2. The gas detection device according to claim 1, wherein the first surface and the second surface at the first open end have a first predetermined distance defined therebetween, the first surface and the second surface at the second open end have a second predetermined distance defined therebetween, and the second predetermined distance is larger than the first predetermined distance.

3. The gas detection device according to claim 1, the projection light is reflected by the first surface and the second surface to form a received light projected onto and received by the optical sensing module, the projection light and the first central axis have a projection angle defined therebetween, the optical sensing module has a second central axis, the received light and the second central axis have a receiving angle defined therebetween.

4. The gas detection device according to claim 3, wherein the projection light is reflected between the first surface and the second surface for N times, the first central axis is parallel to a horizontal axis, an inclined angle is defined between the first surface and the horizontal axis and between the second surface and the horizontal axis, the receiving angle between the received light and the second central axis satisfies $\beta=\alpha-2\gamma N$, wherein $\alpha$ is the projection angle, $\beta$ is the received angle, $\gamma$ is the inclined angle, and N is the number of the times of reflection.

5. The gas detection device according to claim 1, wherein a slope of the first surface adjacent to the first open end is the same as a slope of the first surface adjacent to the second open end, and a slope of the second surface adjacent to the first open end is the same as a slope of the second surface adjacent to the second open end.

6. The gas detection device according to claim 1, wherein the sampling chamber further comprises a third surface and a fourth surface corresponding to the third surface, the third surface and the fourth surface are disposed between the first open end and the second open end, the first surface, the second surface, the third surface and the fourth surface are connected to each other sequentially, and the third surface and the fourth surface are not parallel to each other.

7. The gas detection device according to claim 6, wherein the third surface and the fourth surface at the first open end have a third predetermined distance defined therebetween, the third surface and the fourth surface at the second open end have a fourth predetermined distance defined therebetween, and the fourth predetermined distance is larger than the third predetermined distance.

8. The gas detection device according to claim 1, wherein the chamber module further comprises a light guiding portion disposed between the sampling chamber and the receiving chamber, the light guiding portion has a light guiding surface, the projection light is reflected by the first surface and the second surface for forming an incident light projected onto the guiding surface, the incident light is reflected by the light guiding surface for forming a received light projected onto and received by the optical sensing module, the projection light and the first central axis have a projection angle defined therebetween, the incident light and the first central axis have an incident angle defined therebetween, the optical sensing module has a second central axis, the received light and the second central axis have a receiving angle defined therebetween.

9. The gas detection device according to claim 8, wherein the light guiding surface inclines for a predetermined angle relative to a horizontal axis, the projection light is reflected N times between the first surface and the second surface, the first central axis is parallel to the horizontal axis, an inclined angle is defined between the first surface and the horizontal axis, and between the second surface and the horizontal axis, the incident angle between the incident light and the first central axis satisfies $\lambda=\alpha-2\gamma N$, wherein $\alpha$ is the projection angle, $\lambda$ is the degree of the incident angle, $\gamma$ is the degree of the inclined angle, and N is the number of times of reflection.

10. The gas detection device according to claim 1, wherein the chamber module further comprises a light guiding portion disposed between the sampling chamber and the receiving chamber, the second surface adjacent to the second open end and the optical sensing module have a predetermined height defined therebetween, the predetermined height and the second predetermined distance satisfy $(0.8*L2) \leq H \leq (3*L2)$, wherein H is the predetermined height and L2 is the second predetermined distance.

11. The gas detection device according to claim 1, wherein the chamber module further comprises a light guiding portion disposed between the sampling chamber and the receiving chamber, the light guiding portion has a light guiding surface, the light guiding surface inclines for a predetermined angle of from 30 to 60 degrees relative to a horizontal axis.

12. The gas detection device according to claim 1, wherein the chamber module further comprises a light guiding portion disposed between the sampling chamber and the receiving chamber and an open slot, the open slot is connected between the light guiding portion and the receiving chamber and has a predetermined width, the second surface of the sampling chamber and the optical sensing module has a predetermined height defined therebetween, the predetermined width and the predetermined height satisfy $(0.8*W) \leq H \leq (3*W)$, wherein H is the predetermined height and W is the predetermined width.

13. The gas detection device according to claim 1, wherein the sampling chamber further comprises a gas diffusion tank disposed between the first open end and the second open end.

14. The gas detection device according to claim 1, wherein the light emitting module is an infrared light emitter and the optical sensing module is an infrared optical sensor.

15. A gas detection device comprising:

a chamber module comprising a light condensing chamber, a receiving chamber and a sampling chamber connected between the light condensing chamber and the receiving chamber;

a light emitting module disposed on the light condensing chamber for generating a light; and an optical sensing module disposed in the receiving chamber;

wherein the sampling chamber comprises a first open end, a second open end opposite to the first open end, a first surface, a second surface opposite to the first surface, a third surface and a fourth surface opposite to the third surface;

wherein the first open end is connected to the light condensing chamber, the second open end is connected to the receiving chamber, the first surface, the second surface, the third surface and the fourth surface are disposed between the first open end and the second open end and are connected to each other sequentially, the first surface is not parallel to the second surface, and the third surface is not parallel to the fourth surface;

wherein the light comprises a first projection light projected onto the first surface and a second projection light projected onto the third surface, the first projection light is reflected by the first surface and the second surface for forming a first received light projected onto and received by the optical sensing module, the second projection light is reflected by the third surface and the fourth surface for forming a second received light projection onto and received by the optical sensing module, the light emitting module has a first central axis, the first projection light and the first central axis have a first projection angle defined therebetween, the second projection light and the first central axis have a second projection angle defined therebetween, the optical sensing module has a second central axis, the first received light and the second central axis have a first receiving angle defined therebetween, and the second received light and the second central axis have a second receiving angle defined therebetween.

16. The gas detection device according to claim 15, wherein the first projection light is reflected for $N_1$ times between the first surface and the second surface, the second projection light is reflected for $N_2$ times between the third surface and the fourth surface, the first central axis is parallel to a horizontal axis, a first inclined angle is defined between the third surface and the horizontal axis and between the second surface and the horizontal axis, a second inclined angle is defined between the third surface and the horizontal axis and between the fourth surface and the horizontal axis, the first receiving angle between the first received light and the second central axis satisfy $\beta_1=\alpha_1-2\gamma_1 N_1$, and the second receiving angle between the second received angle and the second central axis satisfy $\beta_2=\alpha_2-2\gamma_2 N_2$, wherein $\alpha_1$ is the first projection angle, $\alpha_2$ is the first projection angle, $\beta_1$ is the first receiving angle, $\beta_2$ is the second receiving angle, $\gamma_1$ is the first inclined angle, $\gamma_2$ is the second inclined angle, $N_1$ is the times of reflection of the first projection light between the first surface and the second surface, and $N_2$ is the number of times of reflection of the second projection light between the third surface and the fourth surface.

17. The gas detection device according to claim 15, wherein the slope of the first surface adjacent to the first open end is equal to the slope of the first surface adjacent to the second open end, and the slope of the second surface adjacent to the first open end is equal to the slope of the second surface adjacent to the second open end.

* * * * *